United States Patent
Ishizu

(10) Patent No.: US 12,347,549 B2
(45) Date of Patent: Jul. 1, 2025

(54) ELECTRIC EQUIPMENT THAT ASSISTS REGISTRATION OPERATION FOR ASSOCIATING PHOTOGRAPHED IMAGE DATA AND PATIENT INFORMATION, METHOD OF CONTROLLING SAME, AND STORAGE MEDIUM

(71) Applicant: CANON KABUSHIKI KAISHA, Tokyo (JP)

(72) Inventor: Satoshi Ishizu, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 400 days.

(21) Appl. No.: 18/146,651

(22) Filed: Dec. 27, 2022

(65) Prior Publication Data
US 2023/0207104 A1     Jun. 29, 2023

(30) Foreign Application Priority Data
Dec. 27, 2021   (JP) ................................ 2021-212511

(51) Int. Cl.
G16H 30/20     (2018.01)
G06V 40/20     (2022.01)
G16H 10/60     (2018.01)

(52) U.S. Cl.
CPC ............. *G16H 30/20* (2018.01); *G06V 40/25* (2022.01); *G16H 10/60* (2018.01)

(58) Field of Classification Search
CPC ........ G16H 30/20; G16H 10/60; G16H 40/63; G06V 40/25
See application file for complete search history.

(56) References Cited

U.S. PATENT DOCUMENTS

| | | | |
|---|---|---|---|
| 2011/0231101 A1* | 9/2011 | Bidargaddi | A61B 5/1118 702/19 |
| 2018/0184907 A1* | 7/2018 | Tran | G08B 21/0446 |
| 2020/0267551 A1* | 8/2020 | Tao | H04W 12/068 |
| 2021/0312079 A1* | 10/2021 | Nishida | G16H 10/40 |
| 2022/0071535 A1* | 3/2022 | Jernigan | A61B 5/0205 |

(Continued)

FOREIGN PATENT DOCUMENTS

| | | |
|---|---|---|
| JP | 4344956 A | 10/2009 |
| JP | 4745974 A | 8/2011 |

*Primary Examiner* — Iriana Cruz
(74) *Attorney, Agent, or Firm* — Carter, DeLuca & Farrell LLP

(57) ABSTRACT

An examination assisting apparatus capable of preventing an error in a registration operation performed by an user for associating photographed image data of an affected area of a patient with patient information. A user acquires patient information by reading a patient identifier and holds the same in a storage medium, and generates and stores photographed image data in association with the patient information stored in the storage medium. Walking information of a walk of the user is acquired. Notification to the user is performed based on the walking information. Photographing by an image capturing operation is stopped based on the walking information. The patient information is deleted from the storage medium based on an operation by the user in response to the notification. The notification is terminated in a case where the patient information is deleted from the storage medium.

14 Claims, 11 Drawing Sheets

(56) References Cited

U.S. PATENT DOCUMENTS

| | | | |
|---|---|---|---|
| 2022/0075989 A1* | 3/2022 | Kimhi | G06V 40/167 |
| 2023/0156245 A1* | 5/2023 | Resnick | H04N 21/23418 |
| | | | 725/109 |

* cited by examiner

*FIG. 6*

| ITEM | INFORMATION | |
|---|---:|---|
| PATIENT INFORMATION (NAME & ID) | TARO SATO, 001 | ~600 |
| POLLING INTERVAL (MILLISECONDS) | 1000 | ~601 |
| NUMBER OF DETECTED STEPS (STEPS) | 7 | ~602 |
| DETECTED WALKING TIME (SECONDS) | 5 | ~603 |
| WALKING DETECTION DETERMINATION RESULT (BOOL) | FALSE | ~604 |
| NO-OPERATION DETECTION TIME (SECONDS) | 10 | ~605 |
| PHOTOGRAPHING MODE AT TIME OF DETECTING WALK | MANUAL | ~606 |
| NUMBER OF TIMES OF OPERATION OF RELEASE BUTTON AFTER DETECTING WALK (TIMES) | 3 | ~607 |
| SETTING HOLD DETERMINATION RESULT (BOOL) | FALSE | ~608 |

ELECTRIC EQUIPMENT THAT ASSISTS REGISTRATION OPERATION FOR ASSOCIATING PHOTOGRAPHED IMAGE DATA AND PATIENT INFORMATION, METHOD OF CONTROLLING SAME, AND STORAGE MEDIUM

BACKGROUND OF THE INVENTION

Field of the Invention

The present invention relates to an electric equipment, a method of controlling the same, and a storage device, and more particularly to an electric equipment that assists a registration operation for associating image data, photographed for examination, of an affected area and patient information, a method of controlling the same, and a storage device.

Description of the Related Art

Conventionally, to manage changes in the condition of a patient, an affected area of the patient is photographed by a user (e.g. a nurse) using a camera every day. However, in a medical site, there is a problem that an error often occurs in a registration operation for associating photographed image data of an affected area and examination-related information (patient information, such as the name of a patient and a medical record number). Examples of such a registration operation error include recording omission, erroneous recording, and misidentification of a patient.

There are several conventional techniques for preventing such a registration operation error. For example, in a known technique for preventing a registration operation error, as disclosed e.g. in Japanese Patent No. 4344956, whenever a patient to be photographed changes and a camera operated by a user reads a patient identifier (such as a barcode), patient information is displayed on a display of the camera, thereby facilitating visual confirmation of the patient information. Further, in another known technique for preventing such a registration operation error, as disclosed e.g. in Japanese Patent No. 4745974, whether or not a patient to be photographed has changed is detected using the photographing position of a camera and the position of a patient, which are determined based on GPS information.

However, the technique disclosed in Japanese Patent No. 4344956 has a problem that if omission occurs in the operation of the examining person, for reading a patient identifier (such as a barcode) using the camera, visual confirmation of the patient number of the patient to be photographed is also omitted, and in this case, it is impossible to prevent the registration operation error. This problem is liable to occur in a case where a user photographs patients, one after another, while making rounds in the same room.

Further, the sufficient GPS measurement accuracy cannot be ensured in a hospital (indoors). For this reason, even when it is determined that the photographing position of the camera has changed based on the GPS information, it is difficult for the technique disclosed in Japanese Patent No. 4745974 to distinguish between a change caused by movement of the user and a change caused by a measurement error of the GPS, and hence it is difficult to detect a change of a patient to be photographed with high accuracy. Particularly, in the case where the examining person photographs patients, one after another, while making rounds in the same room, this problem becomes pronounced.

SUMMARY OF THE INVENTION

The present invention provides an electric equipment that is capable of preventing an error in a registration operation performed by a user for associating photographed image data of an affected area of a patient with patient information, when the user moves to change a patient to be photographed, a method of controlling the same, and a storage medium.

In a first aspect of the present invention, there is provided an electric equipment that has a function of acquiring patient information of an identifier according to an operation by a user and storing the acquired patient information in a storage medium, a function of generating photographed image data through photographing according to an operation by the user, and a function of storing the photographed image data in association with the patient information stored in the storage medium, including at least one processor, and a memory coupled to the at least one processor, the memory having instructions that, when executed by the processor, configure the processor of the electric equipment to: acquire walking information of a walk of the user, perform notification to the user based on the walking information, stop photographing by an image capturing operation based on the walking information, delete the patient information from the storage medium based on an operation by the user in response to the notification, and terminate the notification in a case where the patient information is deleted from the storage medium.

In a second aspect of the present invention, there is provided a method of controlling an electric equipment that has a function of acquiring patient information of an identifier according to an operation by a user and storing the acquired patient information in a storage medium, a function of generating photographed image data through photographing according to an operation by the user, and a function of storing the photographed image data in association with the patient information stored in the storage medium, including acquiring walking information of a walk of the user, performing notification to the user based on the walking information, stopping photographing by an image capturing operation based on the walking information, deleting the patient information from the storage medium based on an operation by the user in response to the notification, and terminating the notification in a case where the patient information is deleted from the storage medium.

According to the present invention, it is possible to prevent an error in a registration operation performed by a user for associating photographed image data of an affected area of a patient with patient information, when the user moves to change a patient to be photographed.

Further features of the present invention will become apparent from the following description of exemplary embodiments (with reference to the attached drawings).

BRIEF DESCRIPTION OF THE DRAWINGS

FIG. 6 is a table showing an example of camera settings stored in a camera's internal storage medium.

DESCRIPTION OF THE EMBODIMENTS

The present invention will now be described in detail below with reference to the accompanying drawings showing embodiments thereof.

Figure 1:
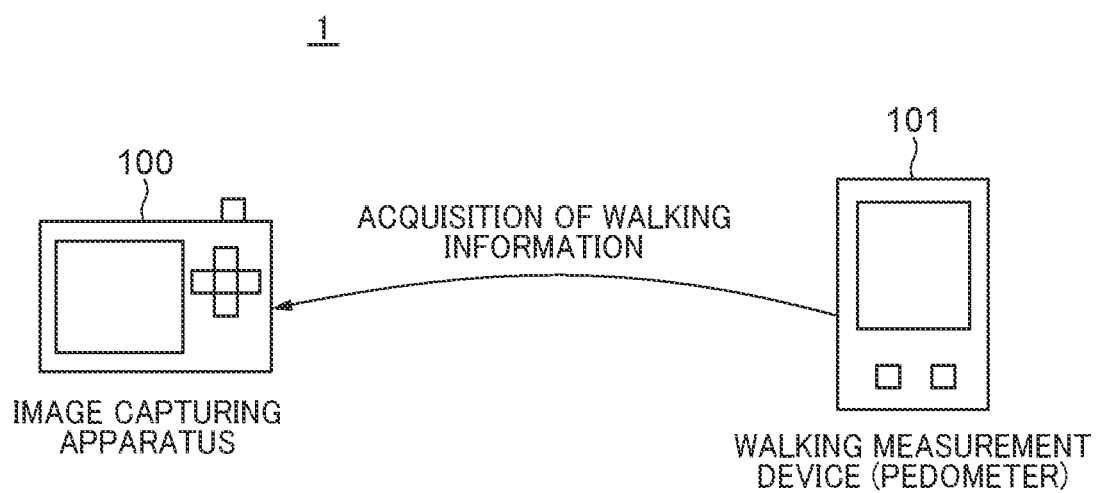
FIG. 1 is an entire configuration diagram of a system including an image capturing apparatus, as an electric equipment according to an embodiment of the present invention, which detects a walk of a user and notifies the user of a detection result.

FIG. 1 is an entire configuration diagram of a system 1 including an image capturing apparatus 100 as an electric equipment for assisting medical testing according to an embodiment of the present invention, which detects a walk of a user and notifies the user of a detection result.

Referring to FIG. 1, the system 1 includes the image capturing apparatus 100 and a walking measurement device 101 that are capable of performing wireless communication with each other.

When a user performs a photographing operation, more specifically, presses a release button 501 (see FIG. 5), the image capturing apparatus 100 photographs an affected area of a patient to generate photographed image data. Further, the image capturing apparatus 100 reads and acquires patient information, such as a patient management number, which is associated with a patient, from a predetermined identifier, such as a barcode, which is printed e.g. on a wristband that the patient wears on his/her arm, or the like, using a patient information acquisition function, described hereinafter. The image capturing apparatus 100 stores the photographed image data of the affected area of the patient in association with this acquired patient information. Further, similar to a commercially available digital camera, the image capturing apparatus 100 includes an acceleration sensor and a gyro sensor which are capable of detecting a vertically moving state and a horizontally moving state. Simultaneously when the image capturing apparatus 100 is powered on, the image capturing apparatus 100 becomes capable of wirelessly communicating with the walking measurement device 101 and maintains the state communicable with the walking measurement device 101 until the image capturing apparatus 100 is powered off.

Similar to a commercially available walking measurement device (pedometer), the walking measurement device 101 (external device) detects a walk and counts walking information (such as the number of steps and walking time). Further, the walking measurement device 101 is capable of performing wireless communication with the image capturing apparatus 100 according e.g. to the wireless communication standard Bluetooth Low Energy (BLE). After wireless communication with the image capturing apparatus 100 is established, the walking measurement device 101 transmits the walking information to the image capturing apparatus 100.

Note that in the present embodiment, an example will be described in which, in the system 1, after wireless communication is established between with the image capturing apparatus 100 and the walking measurement device 101, the walking information is transmitted and received therebetween. However, this is not limitative, but it is only required that the walking information can be transmitted and received between the image capturing apparatus 100 and the walking measurement device 101. For example, the form of connection between the image capturing apparatus 100 and the walking measurement device 101 may be wired connection, and further, the function (first detection unit) of the walking measurement device 101 may be provided within the image capturing apparatus 100.

Figure 2:
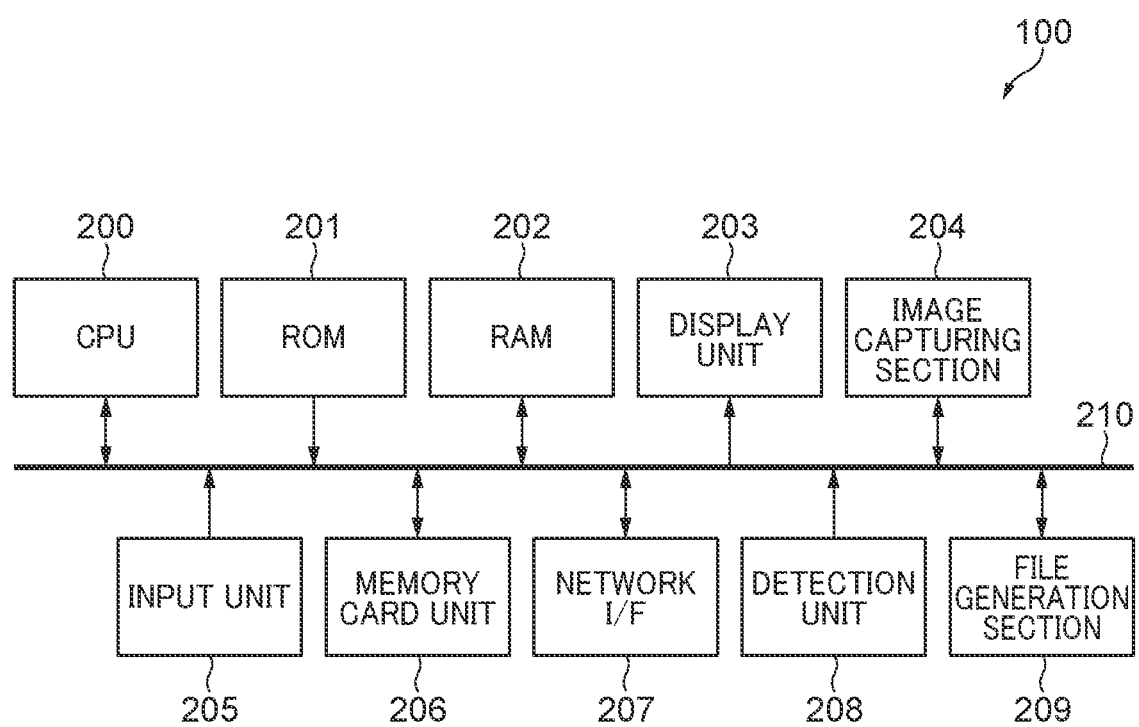
FIG. 2 is a block diagram showing a hardware configuration of the image capturing apparatus.

FIG. 2 is a block diagram showing a hardware configuration of the image capturing apparatus 100.

The image capturing apparatus 100 is a digital still camera and realizes an image capturing process described below by executing a predetermined control program.

Referring to FIG. 2, the image capturing apparatus 100 includes a CPU 200, a ROM 201, a RAM 202, a display unit 203, an image capturing section 204, an input unit 205, and a memory card unit 206. The image capturing apparatus 100 further includes a network interface 207, a detection unit 208, a file generation section 209, and a system bus 210.

The CPU 200 controls the overall operation of the digital still camera.

The ROM 201 stores programs for operation processes of the CPU 200 (such as programs for performing processing when the digital still camera is powered on and basic input/output processing).

The RAM 202 functions as a main memory for the CPU 200. A variety of programs including control programs for realizing processes, described hereinafter, are loaded e.g. from the ROM 201 into the RAM 202 and executed by the CPU 200. Further, the RAM 202 provides a work area when the CPU 200 executes a variety of processes.

The display unit 203 performs a variety of displays under the control of the CPU 200. For example, the display unit 203 displays a live view of an object to be imaged and data stored in a storage medium.

The image capturing section 204 reads an optical image using a solid-state image sensor and generates electrical image data by performing analog-to-digital conversion.

The input unit 205 is comprised of buttons for performing a variety of operations, including the release button 501 (see FIG. 5) disposed on an upper portion of the image capturing apparatus 100.

The memory card unit 206 has a removable storage medium inserted therein and enables data to be stored in the removable storage medium and the stored data to be read from the removable storage medium.

The network interface 207 (communication unit) is connected e.g. to a server computer, a personal computer, the walking measurement device 101, and so forth, for transmission and reception of data.

The detection unit 208 (second detection unit) is comprised of a biaxial acceleration sensor for detecting horizontal movement and an angular speed sensor (gyro sensor).

The file generation section 209 converts image data generated by the image capturing section 204 to image data in a general-purpose still image format (image data in the JPEG format in the present embodiment) under control of the CPU 200.

The system bus 210 is comprised of an address bus, a data bus, and a control bus, which connect between the components described above.

Figure 3:
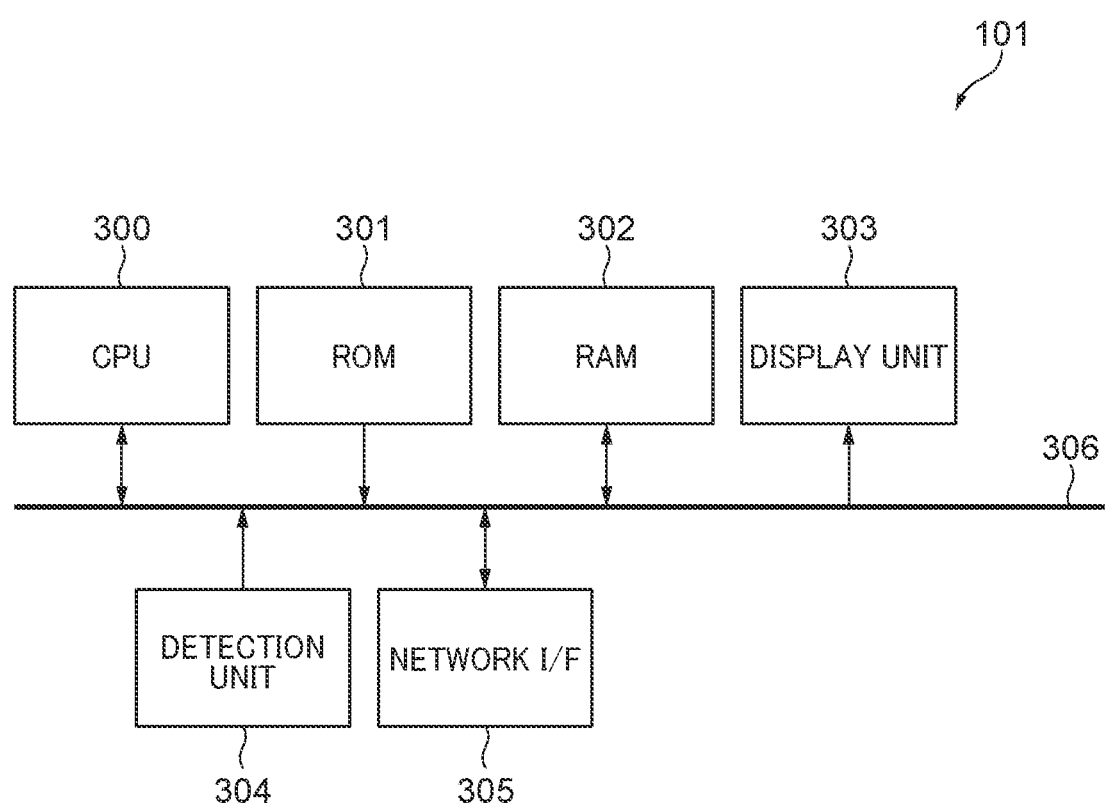
FIG. 3 is a block diagram showing a hardware configuration of a walking measurement device appearing in FIG. 1.

FIG. 3 is a block diagram showing a hardware configuration of the walking measurement device 101.

The walking measurement device 101 is a pedometer and realizes measurement of the number of steps, as described below, by executing a predetermined control program.

Referring to FIG. 3, the walking measurement device 101 includes a CPU 300, a ROM 301, a RAM 302, a display unit 303, a detection unit 304, a network interface 305, and a system bus 306.

The CPU 300 controls the overall operation of the walking measurement device.

The ROM 301 stores programs for operation processes of the CPU 300 (such as programs for performing processing when the walking measurement device is powered on and basic input/output processing).

The RAM 302 functions as a main memory for the CPU 300. A variety of programs including control programs for realizing processes, described hereinafter, are loaded e.g. from the ROM 301 into the RAM 302 and executed by the CPU 300. Further, the RAM 302 provides a work area when the CPU 300 executes a variety of processes.

The display unit 303 performs a variety of displays under the control of the CPU 300. For example, the display unit 303 displays walking information stored in the RAM 302.

The detection unit 304 is comprised of e.g. a triaxial acceleration sensor for detecting a walking motion, and is worn by a person to be measured (such as a user), for measurement of acceleration of motion of the person.

The network interface 305 is connected e.g. to a server computer, a personal computer, and the above-mentioned image capturing apparatus 100, for transmission and reception of walking information.

The system bus 306 is comprised of an address bus, a data bus, and a control bus, which connect between the components described above.

Figure 4:
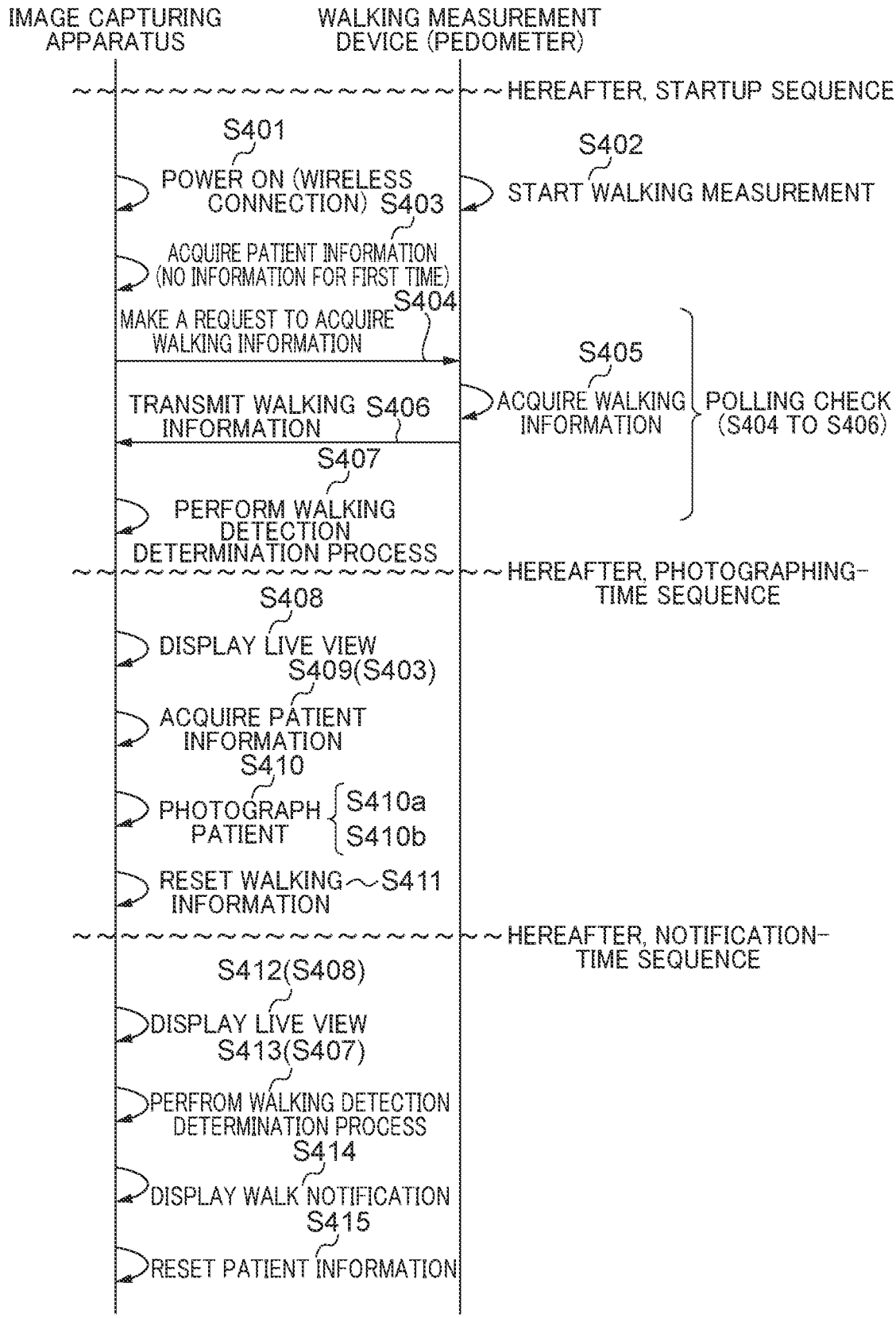
FIG. 4 is a sequence diagram of an examination process performed by the system shown in FIG. 1.

FIG. 4 is a sequence diagram of an examination process performed by the system 1.

With reference to FIG. 4, the outline of the examination process will be described, and details of the examination process will be described with reference to FIG. 7 et seq.

First, a startup sequence from a step S401 to a step S407 is performed.

In the step S401, the image capturing apparatus 100 is powered on by a user (such as a nurse), the CPU 200 of the image capturing apparatus 100 establishes wireless communication with the walking measurement device 101 using the above-mentioned connection method (such as the BLE connection).

In the step S402, when wireless communication with the image capturing apparatus 100 is established, the CPU 300 of the walking measurement device 101 starts walking measurement. Note that the walking information (such as the number of steps and the walking time) stored by the walking measurement device 101 in the RAM 302 may be initialized when wireless communication is established in the step S401. Further, the CPU 200 may acquire the walking information from the walking measurement device 101 when wireless communication is established in the step S401 and store the acquired information in a camera's internal storage medium, referred to below.

In the step S403, the CPU 200 acquires patient information from a storage section within the image capturing apparatus 100 (hereinafter referred to as the "camera's internal storage medium"), such as the RAM 202 or the memory card unit 206. However, patient information does not exist in either of the RAM 202 or the memory card unit 206 of the image capturing apparatus 100 during execution of the startup sequence started immediately after the image capturing apparatus 100 is powered on. Note that the image capturing apparatus 100 has the patient information acquisition function of acquiring, when a user sets the image capturing apparatus 100 to a live view mode and a barcode or the like printed e.g. on a wristband of a patient is displayed on the live view image on the display unit 203, the patient information from the displayed barcode. The CPU 200 stores the patient information acquired by the patient information acquisition function by writing the acquired information into the RAM 202 or the memory card unit 206 and prepares for acquisition of patient information next time.

In the step S404, the CPU 200 (acquisition unit) transmits a request to acquire walking information to the walking measurement device 101. This request is, for example, performed by using a GET method which is one of HTTP request methods.

In the step S405, to respond to the request to acquire walking information, which is received in the step S404, the CPU 300 acquires the walking information stored in the RAM 302 which is updated as an occasion arises after the walking measurement is started in the step S402.

In the step S406, the CPU 300 transmits the walking information acquired in the step S405 to the image capturing apparatus 100.

Note that processing in the steps S404 to S406 (hereinafter referred to as the "polling check") is periodically executed while the image capturing apparatus 100 is in the power-on state.

In the step S407, the CPU 200 performs a walking detection determination process for determining whether or not the user has walked, based on the walking information acquired by the polling check and the like. Although details of this process will be described hereinafter, by executing this process, it is possible to determine, based on a difference in the walking information, whether or not the user has walked after photographing of a patient is performed last time in a step S410, described hereinafter. Not that in the step S407 performed in the startup sequence in which photographing of a patient has not been performed, the CPU 200 determines that the user has not walked and starts a photographing-time sequence described below.

In the photographing-time sequence, the following steps S408 to S411 are performed.

In a step S408, the CPU 200 displays a live view of an object to be imaged on the display unit 203. At this time, the user starts the patient information acquisition function, by performing a reading operation for adjusting the orientation of the camera such that a barcode or the like indicative of patient information, which is printed on a wristband worn by a patient, is included in the live view. When the patient information acquisition function is started, the patient information is read from the barcode included in the live view and written into the RAM 202 or the memory card unit 206.

In the step S409, the CPU 200 performs patient information acquisition processing. This step (step S409) is the same processing as the above-described step S403. More specifically, the CPU 200 acquires the patient information written in the camera's internal storage medium during the live view display in the step S408 from the camera's internal storage medium. Note that when the patient information acquisition processing in the step S409 is completed, there may be displayed a screen for notifying the user that the user has become capable of performing patient photographing processing which is to be performed in the step S410.

In a step S410a (first half of the step S410), when the release button 501 of the input unit 205 is pressed by the user (an image capturing operation is performed), the CPU 200 photographs the patient, thereby acquiring photographed image data of e.g. an affected area of the patient. The acquired photographed image data of the patient is stored in association with the patient information acquired in the step S409.

In a step S410b (second half of the step S410), similar to the step S407 described above, the CPU 200 performs the walking detection determination process, based on the walking information acquired last time by the polling check, for determining whether or not the user has walked. If it is determined that the user has not walked, the process returns to the step S410a, whereas if it is determined that the user has walked, the process proceeds to a step S411.

As described above, the user performs adjustment of the orientation of the camera during the display of the live view in the step S408 and photographing of a patient to be examined, whereby the user can store photographed image data of the patient and patient information of the patient in a state associated with each other.

In the step S411, the CPU 200 resets the walking information. More specifically, in the present embodiment, the walking information stored in the RAM 302 of the walking measurement device 101 and the walking information stored in the camera's internal storage medium are deleted. Note that the aim of resetting the walking information is to make it possible to determine whether or not the user has walked after photographing of the patient in the step S410 is performed last time. Therefore, although the walking information is deleted in the present embodiment, the walking information stored in the RAM 302 of the walking measurement device 101 or the camera's internal storage medium may not be deleted but may be reset to initial values and the walking information obtained at the time of photographing may be stored by overwriting the initial values.

After that, a notification-time sequence described below is started.

In the notification-time sequence, the following steps S412 to S415 are executed.

In a step S412, similar to the step S408, the CPU 200 performs the live view display. At this time, similar to the step S408, the user can start the patient information acquisition function and write the acquired patient information into the RAM 202 or the memory card unit 206.

In the step S413, similar to the step S407, the CPU 200 performs the walking detection determination process for determining, based on the walking information acquired last time by the polling check, whether or not the user has walked. If it is determined that the user has not walked, the process returns to the step S412, whereas if it is determined that the user has walked, the process proceeds to a step S414.

Next, in the step S414, the CPU 200 (notification unit) displays a notification user interface (UI) 507 (see FIG. 5) indicating that the user has walked, on the display unit 203. Note that details of the notification UI 507 will be described hereinafter. The user using the image capturing apparatus 100 (such as a nurse) views this notification and performs an operation according to the contents of the notification.

In the step S415, the CPU 200 performs processing for resetting the patient information. Note that this step (step S415) is executed in a case where an instruction for deleting the patient information has been provided e.g. based on the notification UI displayed in the step S414. By deleting the patient information from the camera's internal storage medium, it is possible to newly acquire patient information when the photographing-time sequence is started again.

After that, the CPU 200 (termination unit) terminates the display of the notification UI and restarts the photographing-time sequence.

Figure 5:
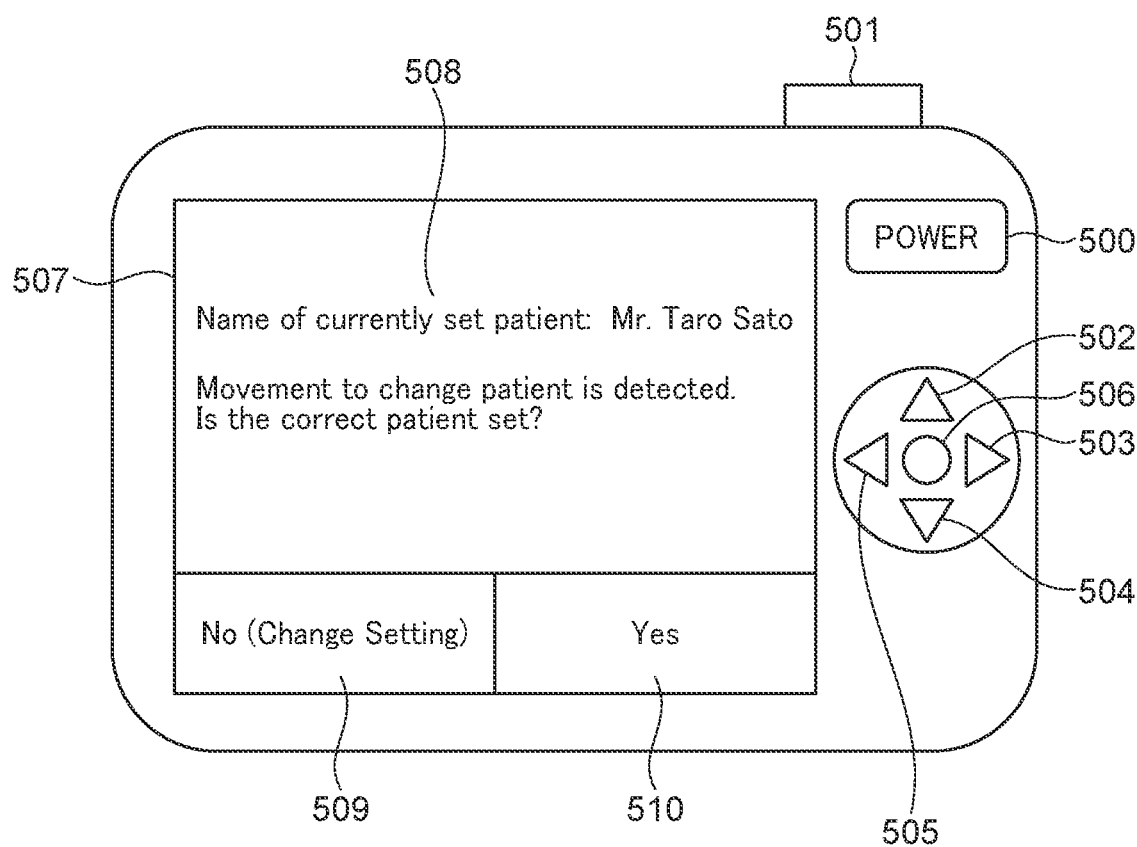
FIG. 5 is a diagram showing an example of a notification user interface displayed in a step in FIG. 4.

FIG. 5 is a diagram showing an example of the notification UI displayed in the step S414 in FIG. 4. Note that as for all of buttons except a power button 500, operations related thereto are described assuming that the image capturing apparatus 100 is in the power-on state.

The image capturing apparatus 100 includes a variety of buttons, shown in FIG. 5, as the components of the input unit 205, and the display unit 203 that displays the notification UI 507.

The power button 500 is used to switch between the power-on state and power-off state of the image capturing apparatus 100. When a user (such as a nurse) presses the power button 500 in the power-off state of the image capturing apparatus 100, the CPU 200 determines that a power-on instruction has been provided from a user and powers on the image capturing apparatus 100. When the user presses the power button 500 in the power-on state of the image capturing apparatus 100, the CPU 200 determines that a power-off instruction has been provided from the user and powers off the image capturing apparatus 100.

The release button 501 is used to give an instruction for photographing a still image to the image forming apparatus 100 and when the user presses the release button 501, the CPU 200 determines that the instruction has been given.

An upward button 502, a rightward button 503, a downward button 504, and a leftward button 505 are used by the user to perform an operation for switching between objects to be selected. In a case where the user presses one of the upward button 502, the rightward button 503, the downward button 504, and the leftward button 505, the CPU 200 determines that an operation for switching one object to be selected to another has been performed by the user on the notification UI 507, described hereinafter, and switches the one object to be selected to the other. A decision button 506 is used by the user to perform a decision operation. In a case where the user presses the decision button 506, the CPU 200 determines that a decision operation has been performed by the user and switches the state of the image capturing apparatus 100 according to the object decided for selection by the decision button 506.

The notification UI 507 is displayed on a touch panel display having both of the function of the display unit 203 and the function of the input unit 205. When the user presses a desired point on a screen of the touch panel display with his/her finger, the CPU 200 determines that an input instruction has been provided from the user to determine what is input from the pressed position, and performs a variety of processing operations, including updating the display.

The notification UI 507 has a message notification area 508, a setting delete button 509, and a setting hold button 510.

The message notification area 508 displays character strings for notifying a user of the situation.

The setting delete button 509 (deletion instructing button) is one of the objects to be selected which can be switched by the user. When a selection decision operation is performed by pressing the decision button 506 in a state in which the setting delete button 509 is selected, the CPU 200 determines that an instruction for deleting patient information has been provided from the user, and deletes the set patient information, from the camera's internal storage medium. Further, also in a case where the setting delete button 509 is pressed by the user with his/her finger, the CPU 200 determines that an instruction for deleting patient information has been provided from the user, and deletes the set patient information, from the camera's internal storage medium.

The setting hold button 510 (holding instructing button) is also one of the objects to be selected which can be switched by a user. When a selection decision operation is performed by pressing the decision button 506 in a state in which the setting hold button 510 is selected, the CPU 200 determines that an instruction for holding patient information has been provided from the user and holds the set patient information in the camera's internal storage medium. Further, also in a case where the setting hold button 510 is pressed by the user with his/her finger, the CPU 200 determines that an instruction for holding patient information has been provided from the user, and holds the set patient information in the camera's internal storage medium.

FIG. 6 is a table showing an example of camera settings stored in the camera's internal storage medium.

The camera settings shown in FIG. 6 are stored in the camera's internal storage medium and used when performing the walking detection determination process in a step S703, a setting hold determination process in a step S706, and a setting delete determination process in a step S708, described hereinafter. In FIG. 6, a description is given only of items of the camera settings, and details of the items will be described with reference to FIG. 7 et seq.

Data 600 indicates patient information. For example, in the data 600, a name and an ID of a patient are managed in a comma-delimited state. The patient information acquired in the above-described steps S403 and S409 in FIG. 4 corresponds to the data 600.

Data 601 indicates a time interval at which walking information is acquired from the walking measurement device 101. In the present embodiment, the data 601 defines an execution interval of the polling check in the steps S404 to S406 in FIG. 4. Note that the polling check is not necessarily required to be executed at the time interval indicated in the data 601, but the data 601 may be used as a reference data of the execution interval, and the polling check may be executed at intervals of a time period indicated in the data 601 at the shortest.

Data 602 indicates a threshold value of the number of steps with reference to which it is determined that the user has walked. In the present embodiment, in a case where the number of steps counted after a patient is photographed last time by the image capturing apparatus 100 is equal to or larger than the threshold value indicated in the data 602, the CPU 200 determines that a walk of the user is detected.

Data 603 indicates a threshold value of the walking time with reference to which it is determined that the user has walked. In the present embodiment, in a case where the walking time counted after a patient is photographed last time by the image capturing apparatus 100 is equal to or larger than the threshold value indicated in the data 603, the CPU 200 determines that a walk of the user is detected.

Data 604 indicates a value indicative of a result of determination of whether or not a walk of the user has been detected (walking detection determination result) by the CPU 200. The value of the walking detection determination result, indicated in the data 604, is used in a step S704, described hereinafter.

Data 605 indicates a threshold value of a no-operation detection time with reference to which it is determined that the user has not operated the image capturing apparatus 100 (no operation). In the present embodiment, in a case where the lapse of time counted after the notification UI 507, described with reference to FIG. 5, is displayed is equal to or larger than the threshold value indicated in the data 605, the CPU 200 determines that no operation is detected and deletes the setting of the patient information.

Data 606 indicates a photographing mode at the time of detecting a walk. More specifically, the data 606 indicates the photographing mode at the time of displaying the notification UI 507, described with reference to FIG. 5. The data 606 is used in determination processing in a step S1006, described hereinafter.

Data 607 indicates a threshold value of the number of times of operation of the release button 501 with reference to which it is determined that the user continues the photographing operation. For example, in a case where the number of times of operation of the release button 501, counted after the notification UI 507 is displayed, is equal to or larger than the threshold value indicated in the data 607, the CPU 200 determines that the user continues the photographing operation, and the patient information in the camera's internal storage medium is held.

Data 608 indicates a value indicative of a result (setting hold determination result) of determination of whether or not to hold the setting of the patient information. The data 608 is used in determination processing in steps S707 and S709, described hereinafter.

The above description has been given of the example of the data held by the image capturing apparatus 100 according to the present embodiment. Note that each data item may be configured to be changeable afterwards by the user (such as a nurse) on the image capturing apparatus 100.

Figure 7:
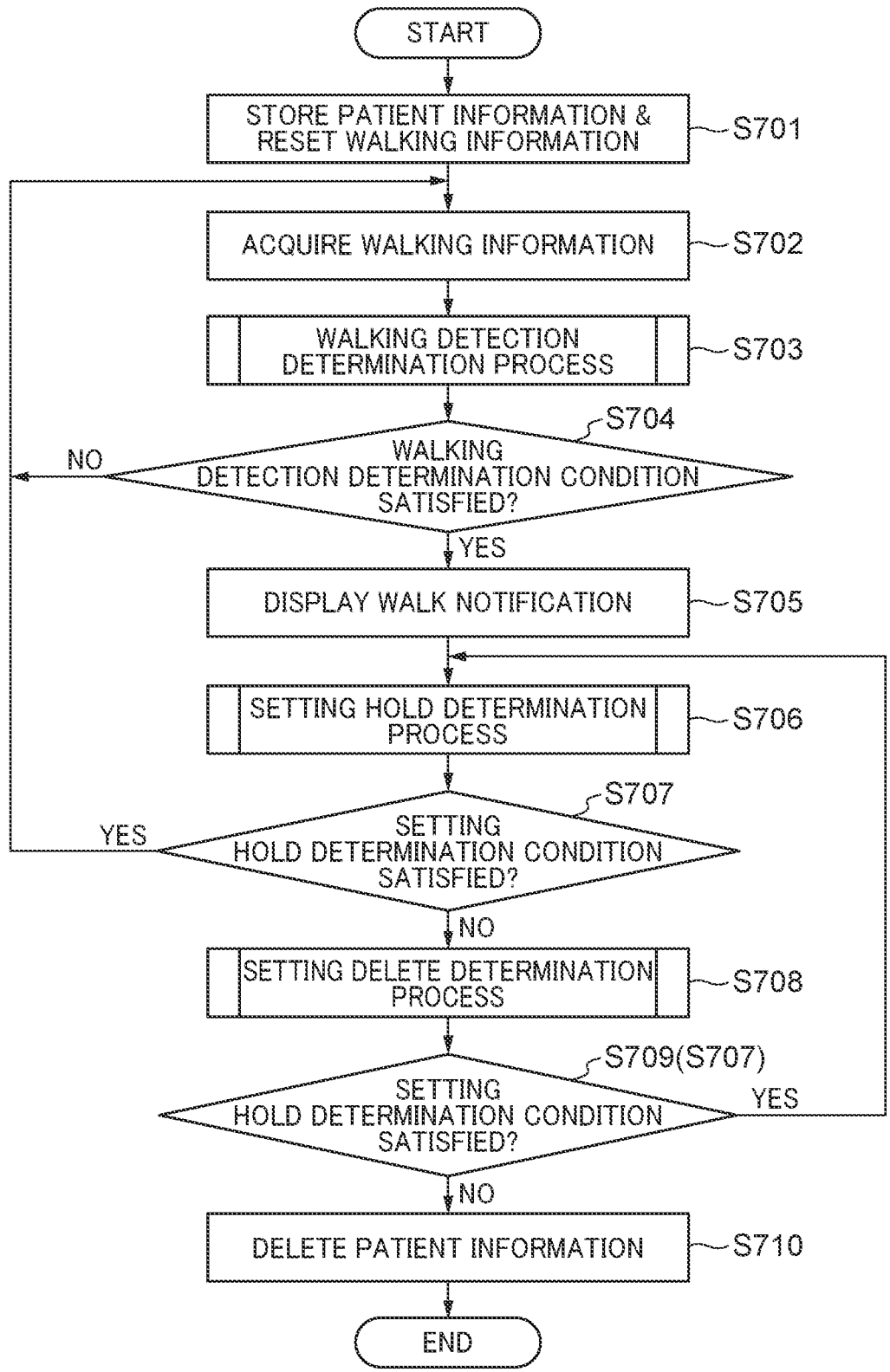
FIG. 7 is a flowchart of a patient information-setting process performed by the image capturing apparatus.

FIG. 7 is a flowchart of a patient information-setting process performed by the image capturing apparatus 100.

Hereafter, with reference to FIG. 7, a detailed description will be given of how the setting of the patient information held in the camera's internal storage medium is manipulated in a case where a walk of the user is detected after photographing a patient, while referring to the notification UI 507 shown in FIG. 5 and the camera settings shown in FIG. 6.

In a step S701, when the patient information acquisition function is started during the live view display, the CPU 200 acquires patient information from a barcode or the like displayed on the live view and stores the acquired patient information in the camera's internal storage medium. This processing corresponds the steps S408 and S409 in FIG. 4. At this time, the patient information is stored in the camera's internal storage medium as the data 600 in FIG. 6. Further, after the patient has been photographed by the user, the walking information stored in the walking measurement device 101 and the camera's internal storage medium is deleted (reset). This processing corresponds the steps S410a, S410b, and S411 in FIG. 4. Then, the process proceeds to a step S702.

In the step S702, the CPU 200 acquires, from the walking measurement device 101, the walking information (such as the number of steps and the walking time) acquired by the last polling check of the walking measurement device 101, and stores the acquired walking information in the RAM 202. Note that there is a fear that after the patient information is stored in the camera's internal storage medium in the step S701, the steps S702 to S704 are repeatedly executed at high speed until any of walking detection determination conditions is satisfied in the step S704, described hereinafter. To avoid this, it is desirable that the execution interval of polling check is set so as not to acquire the information at a time interval shorter than the time interval indicated in the data 601.

In the step S703, the CPU 200 performs the walking detection determination process for determining whether or not the user has walked, using the walking information acquired in the step S702. This process will be described hereinafter in detail with reference to FIG. 8.

In the step S704, the CPU 200 acquires a value of the walking detection determination result indicated in the data 604 and determines whether or not a walk of the user has been detected. On the value of the walking detection determination result, a result of the walking detection determination process in the step S703 is reflected. If it is determined that a walk of the user has been detected (any of the walking detection determination conditions is satisfied), the process proceeds to a step S705, whereas if not, the process returns to the step S702.

In the step S705, the CPU 200 displays the notification UI 507 (see FIG. 5) indicating that a walk of the user has been detected, on the above-described touch panel display. At this time, the CPU 200 starts counting of the number of times of operation of the release button 501 and compares the count with the threshold value indicated in the above-described data 607. This comparison result is used in a step S905 of the setting hold determination process, described hereinafter, with reference to FIG. 9. Further, the CPU 200 stores the photographing mode in the RAM 202 in such a storage form as the data 606. The photographing mode stored in the RAM 202 is used in the step S1006, described hereinafter. Further, the CPU 200 (stopping unit) stops the photographing processing performed by operating the release button 501 during display of the notification UI 507. This makes it possible to prevent photographed image data from being generated in association with the patient information set in the camera's internal storage medium, in spite of the fact that there is a possibility that the patient to be imaged has changed.

In the step S706, the CPU 200 performs the setting hold determination process for determining whether or not to cause the setting of the patient information to remain stored in the camera's internal storage medium, and a result of the setting hold determination process is reflected on the the setting hold determination result indicated by the data 608 in FIG. 6. The present process will be described hereinafter in detail with reference to FIG. 9.

In the step S707, the CPU 200 acquires the value of the setting hold determination result indicated in the data 608 and determines whether or not to cause the setting of the patient information to remain stored in the camera's internal storage medium. On the value of the setting hold determination result, the result of the setting hold determination process in the step S706 is reflected, as mentioned above. If it is determined that the setting of the patient information is to be caused to remain stored in the camera's internal storage medium (any of setting hold determination conditions is satisfied), the process returns to the step S702, whereas if not, the process proceeds to the step S708. Note that in a case where any of the setting hold determination conditions is satisfied, the CPU 200 closes the notification UI 507 displayed in the step S705 and enables the photographing processing to be performed by operating the release button 501.

In the step S708, the CPU 200 performs the setting delete determination process for determining whether or not to delete the setting of the patient information held by the image capturing apparatus 100, and a result of the setting delete determination process is reflected on the the setting hold determination result indicated by the data 608 in FIG. 6. The present process will be described hereinafter in detail with reference to FIG. 10.

In the step S709, the CPU 200 acquires a value of the setting hold determination result indicated in the data 608 and determines whether or not to delete the setting of the patient information held in the camera's internal storage medium. Since the result of the setting delete determination process in the step S708 is reflected on the value of the setting hold determination result, in this step (step S709), the same processing as the step S707 is executed. If it is determined that none of setting delete determination conditions are satisfied, in other words, a setting hold determination condition is satisfied, the process returns to the step S706, whereas if not, the process proceeds to a step S710. Note that in a case where the hold determination condition is not satisfied, the CPU 200 closes the notification UI 507 displayed in the step S705.

In the step S710, the CPU 200 (deletion unit) deletes the patient information stored in the step S701. For example, the CPU 200 deletes the setting of the patient information held in the camera's internal storage medium by overwriting the patient information in the data 600 by null and storing the updated information. Note that when this step (step S710) is finished, the CPU 200 can prepare for photographing of the next patient by starting the photographing-time sequence in FIG. 4 again from the step S408 (live view display).

Figure 8:
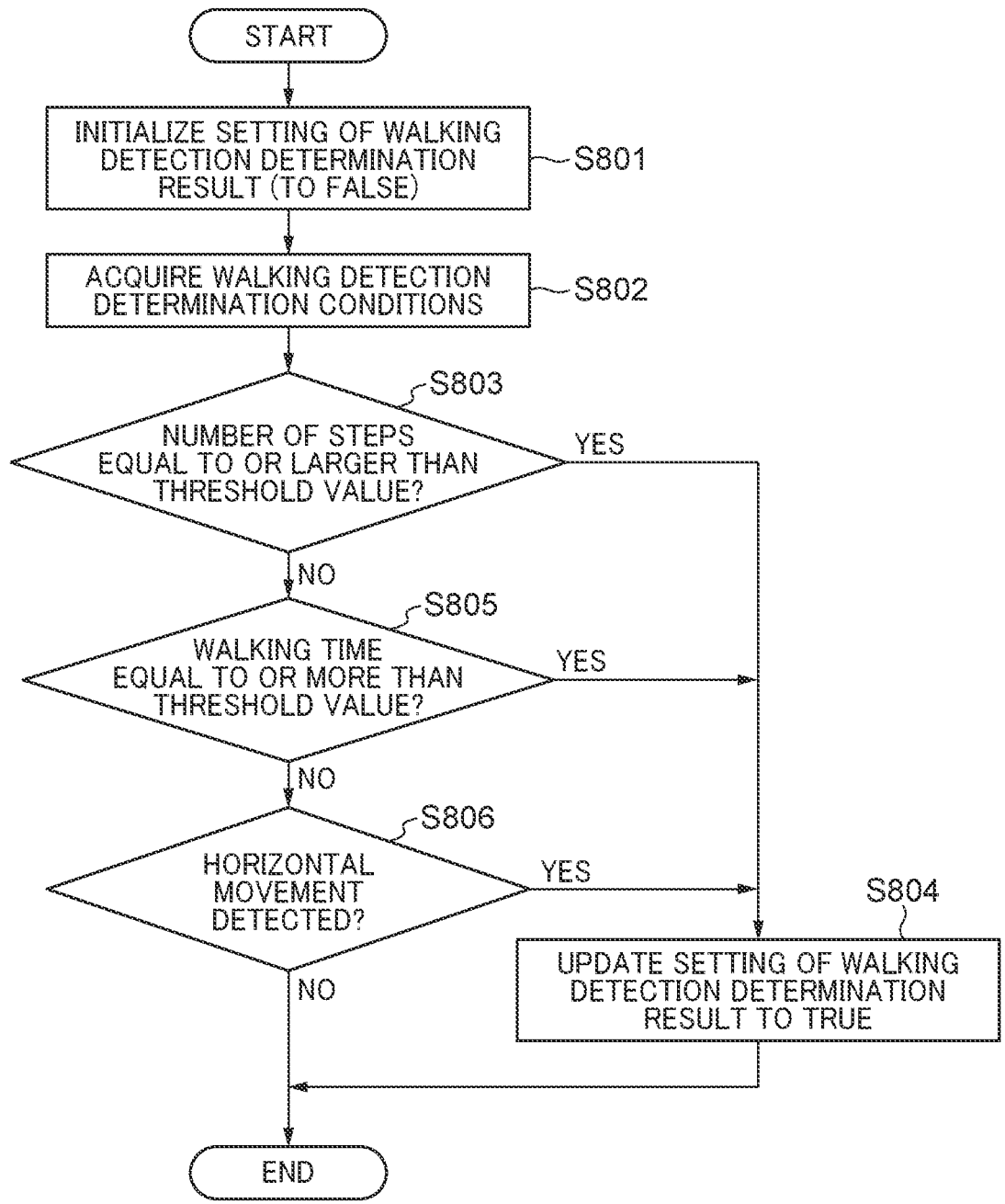
FIG. 8 is a flowchart of a walking detection determination process in a step in FIG. 7.

FIG. 8 is a flowchart of the walking detection determination process in the step S703 in FIG. 7.

The present process will be described below in detail while referring to FIG. 6 (camera settings).

In a step S801, the CPU 200 initializes the value of the walking detection determination result of the data 604 to FALSE.

In a step S802, the CPU 200 acquires, from the camera's internal storage medium, the data 602 which is the threshold value of the number of steps with reference to which it is determined that the user has walked and the data 603 which is the threshold value of the walking time with reference to which it is determined that the user has walked, as the walking detection determination conditions. In the present embodiment, the value of the data 602 (the threshold value of the number of steps) is set to seven (steps), and the value of the data 603 (the threshold value of the walking time) is set to five (seconds).

In a step S803, the CPU 200 compares the number of steps acquired from the walking measurement device 101 in the step S702 and the threshold value (seven) indicated in the data 602 and determines whether or not the user has walked. If the acquired number of steps is equal to or larger than the threshold value, the CPU 200 determines that the user has walked, and the process proceeds to a step S804, whereas if the acquired number of steps is smaller than the threshold value, the CPU 200 determines that the user has not walked, and the process proceeds to a step S805.

In the step S804, the CPU 200 updates the walking detection determination result of the data 604 to TRUE. With this, it is determined in the step S704 in FIG. 7 that any of the walking detection determination conditions is satisfied.

In the step S805, the CPU 200 compares the walking time acquired from the walking measurement device 101 in the step S702 and the threshold value (five seconds) indicated in the data 603 and determines whether or not the user has walked. If the acquired walking time is equal to or more than the threshold value, the CPU 200 determines that the user has walked, and the process proceeds to the step S804, whereas if the acquired walking time is less than the threshold value, the CPU 200 determines that the user has not walked, and the process proceeds to a step S806.

In the step S806, the CPU 200 determines whether or not the image capturing apparatus 100 is in a horizontally moving state. For example, it is possible to determine whether the image capturing apparatus 100 is in the vertically moving state or the horizontally moving state, by using the biaxial acceleration sensor and the angular speed sensor (gyro sensor) that form the detection unit 208. If the image capturing apparatus 100 is in the horizontally moving state, the process proceeds to the step S804, whereas if the image capturing apparatus 100 is not in the horizontally moving state, the present process is terminated, but the process proceeds to the step S704 in FIG. 7. Note that examples of the case where the image capturing apparatus 100 is in the horizontally moving state include a case where the user is moving with a nurse cart on which the image capturing apparatus 100 is placed.

Note that in the present process, the determinations in the steps S803 to S806 are only required to be performed, but the order of executing these steps is not limited to the order described above.

Figure 9:
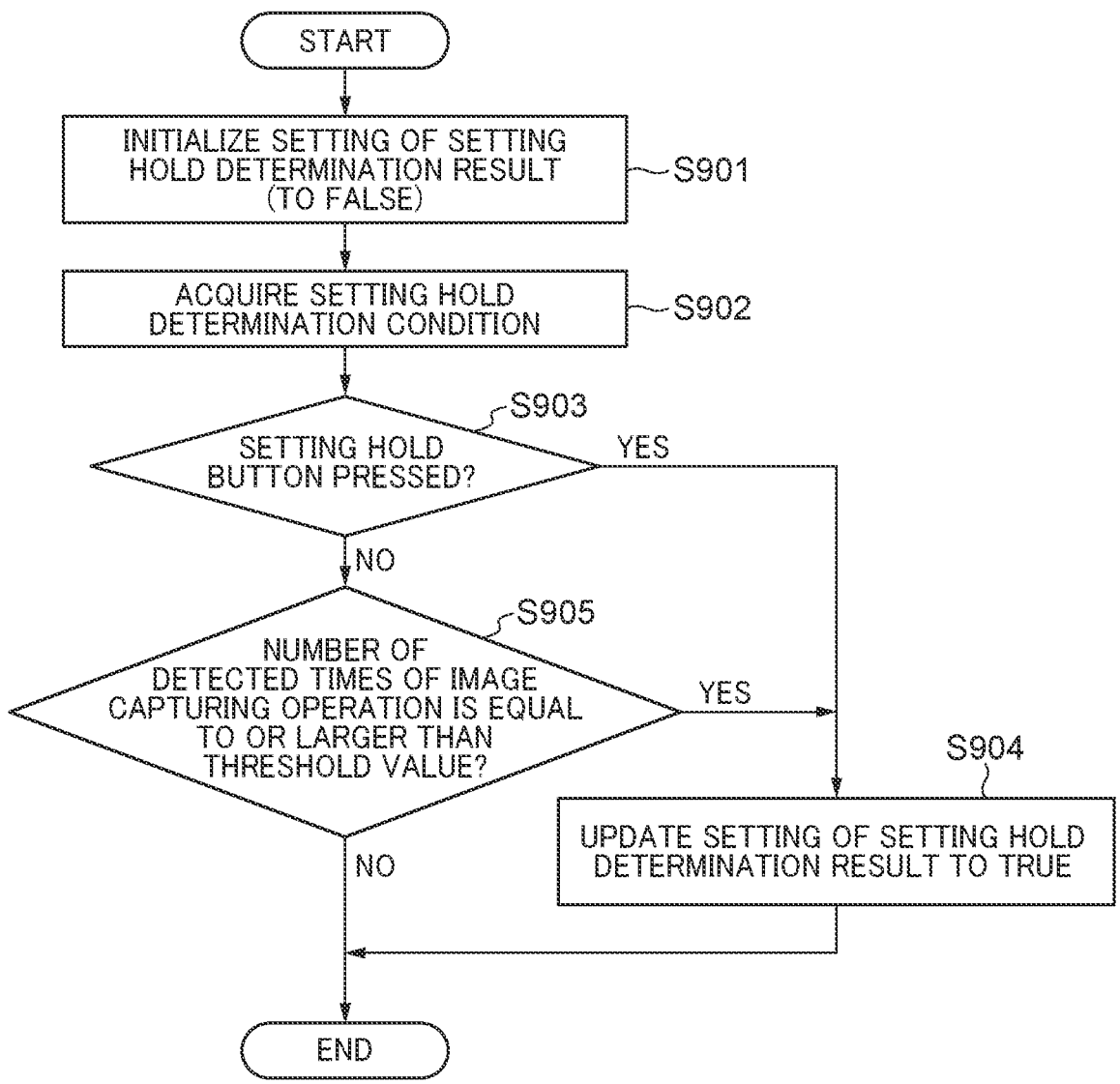
FIG. 9 is a flowchart of a setting hold determination process in a step in FIG. 7.

FIG. 9 is a flowchart of the setting hold determination process in the step S706 in FIG. 7.

The present process will be described below in detail while referring to the notification UI in FIG. 5 and the camera settings in FIG. 6.

In a step S901, the CPU 200 initializes the value of the setting hold determination result of the data 608 to FALSE.

In a step S902, the CPU 200 acquires, from the camera's internal storage medium, the data 607 which is the threshold value of the number of times of operation of the release button 501 with reference to which it is determined that the user continues the photographing operation, as a setting hold determination condition. In the present embodiment, the value of the data 607 (the threshold value of the number of times of pressing of the release button 501) is set to three (times). Note that the value of the data 607 can be changed e.g. by the user on an appropriate basis.

In a step S903, the CPU 200 determines whether or not the setting hold button 510 on the notification UI 507, for receiving an instruction for holding the patient information set in the camera's internal storage medium, has been pressed. If the setting hold button 510 has been pressed, the process proceeds to a step S904, whereas if the setting hold button 510 has not been pressed, the process proceeds to the step S905.

In the step S904, the CPU 200 updates the value of the setting hold determination result of the data 608 to TRUE. With this, it is determined in the step S707 in FIG. 7 that any of the setting hold determination conditions is satisfied.

In the step S905, the CPU 200 determines whether or not the number of times of operation of the release button 501, counted after the notification UI 507 is displayed in the step S705, is equal to or larger than the threshold value indicated in the data 607 (equal to or larger than a predetermined number of times). If the number of times of operation is equal to or larger than the threshold value, the process proceeds to the step S904, whereas if the number of times of operation is smaller than the threshold value, the present process is terminated, but the process proceeds to the above-descried step S707 in FIG. 7.

Figure 10:
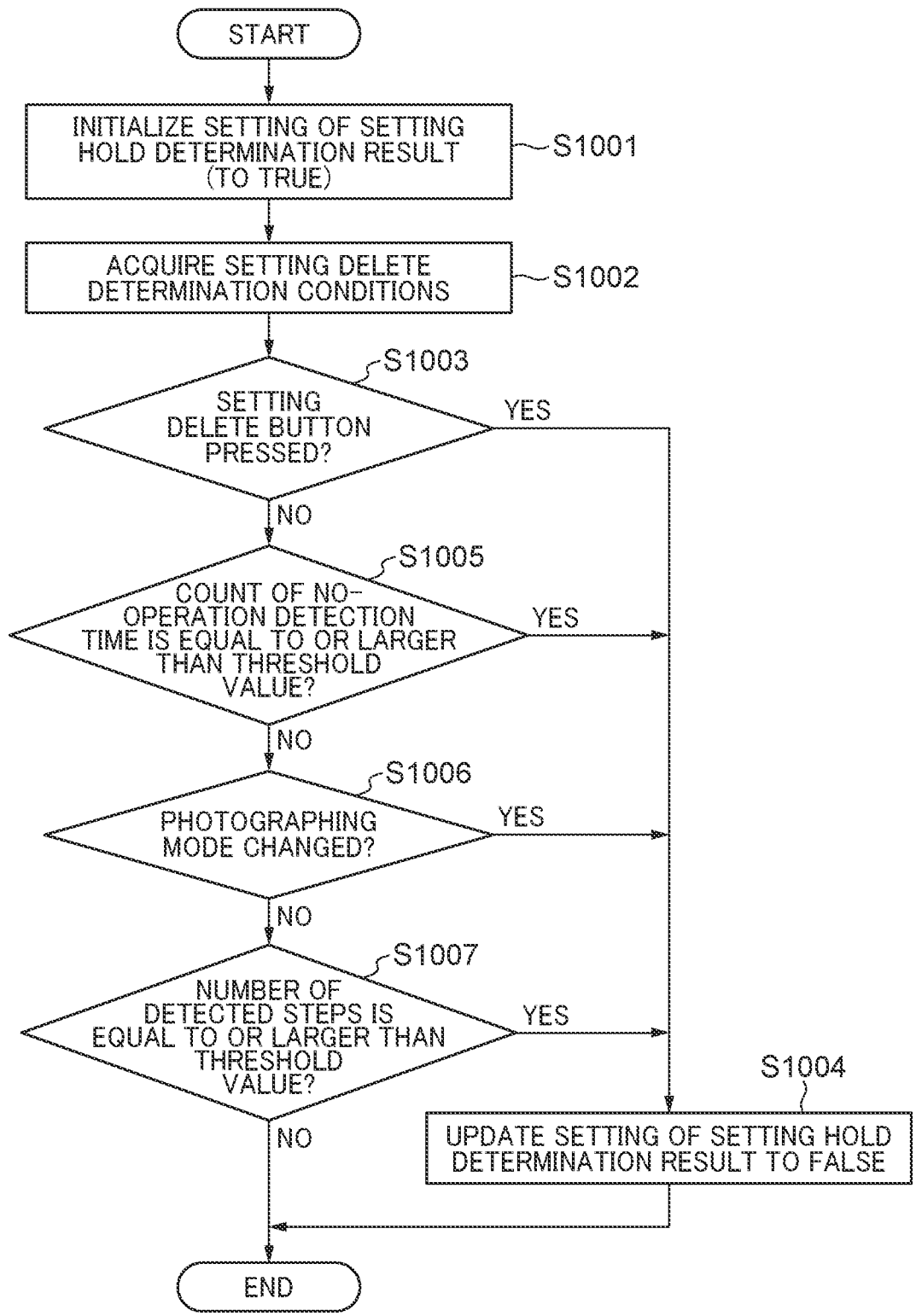
FIG. 10 is a flowchart of a setting delete determination process in a step in FIG. 7.

FIG. 10 is a flowchart of the setting delete determination process in the step S708 in FIG. 7.

The present process will be described below in detail, while referring to the notification UI in FIG. 5 and the camera settings in FIG. 6.

In a step S1001, the CPU 200 initializes the value of the setting hold determination result of the data 608 to TRUE. Note that when the value of the setting hold determination result of the data 608 is initialized in the step S901, the value is set to FALSE. In a case where exclusive control is taken into account, for example, the same data 608 is not used both in the setting hold determination process and the setting delete determination process, but a setting delete determination result may be added to the camera settings in FIG. 6 for use in the setting delete determination process, and the determination of the step S709 may be performed by referring to the setting delete determination result.

In a step S1002, the CPU 200 acquires the threshold value of threshold value of the number of steps, which is indicated in the data 602, the threshold value of the no-operation detection time, which is indicated in the data 605, and the photographing mode at the time of detecting a walk, which is indicated in the data 606, with reference to each of which the setting of the patient information stored in the camera's internal storage medium is determined to be deleted, as the setting delete determination conditions. In the present embodiment, the value of the data 605 (the threshold value of the no-operation detection time) is set to ten (seconds). Note that the value of the data 605 is a value which can be changed e.g. by the user on an appropriate basis.

In a step S1003, the CPU 200 determines whether or not the setting delete button 509 on the notification UI 507, which receives an instruction for deleting the set patient information, from the camera's internal storage medium, has been pressed (a predetermined operation has been performed). If the setting delete button 509 has been pressed, the process proceeds to a step S1004, whereas if the setting delete button 509 has not been pressed, the process proceeds to a step S1005.

In the step S1004, the CPU 200 updates the value of the setting hold determination result of the data 608 to FALSE. With this, it is determined in the above-described step S709 in FIG. 7 that the setting hold determination condition is not satisfied.

In the step S1005, the CPU 200 determines whether or not the count of the no-operation detection time of the image capturing apparatus 100 is equal to or larger than the threshold value of the data 605 (whether no-operation is detected for a predetermined time period or longer). The no-operation detection time of the image capturing apparatus 100 may start to be counted at a timing when the notification UI 507 is displayed in the step S705 in FIG. 7 or at a timing when the image capturing apparatus 100 is operated last time. If the count of the no-operation detection time of the image capturing apparatus 100 is equal to or larger than the threshold value of the data 605, the process proceeds to the step S1004, whereas if not, the process proceeds to the step S1006.

In the step S1006, the CPU 200 determines whether or not the photographing mode has been changed from the time at which the photographing mode is acquired in the step S1002 (a predetermined operation has been performed). If the photographing mode has been changed, the process proceeds to the step S1004, whereas if the photographing mode has not been changed, the process proceeds to a step S1007.

Note that a difference between the steps S1005 and S1006 is that in the step S1005, the process does not immediately proceed to the step S1004 even when the image capturing apparatus 100 is not operated, but in the step S1006, the process immediately proceeds to the step S1004 when the photographing mode is changed. Further, the timing of storing the photographing mode in the data 606 has already been described in the step S705 in FIG. 7 and hence description thereof is omitted.

In the step S1007, the CPU 200 further determines whether or not the user has walked. This determination is executed by the same process as the walking detection determination process in FIG. 8 based on the walking information (the number of steps or the walking time: second walking information) acquired from the walking measurement device 101 by the polling check during display of the notification UI 507. For example, in a case where the value of the data 602 (the threshold value of the number of steps) is set to seven (steps), if a walk of seven steps or more is detected during display of the notification UI 507, it is determined in this step (step S1007) that the user has walked. If the number of detected steps is equal to or larger than the threshold value indicated in the data 602 acquired in the step S1002, the process proceeds to the step S1004, whereas if not, the present process is terminated, but the process proceeds to the above-described step S709 in FIG. 7.

Figure 11:
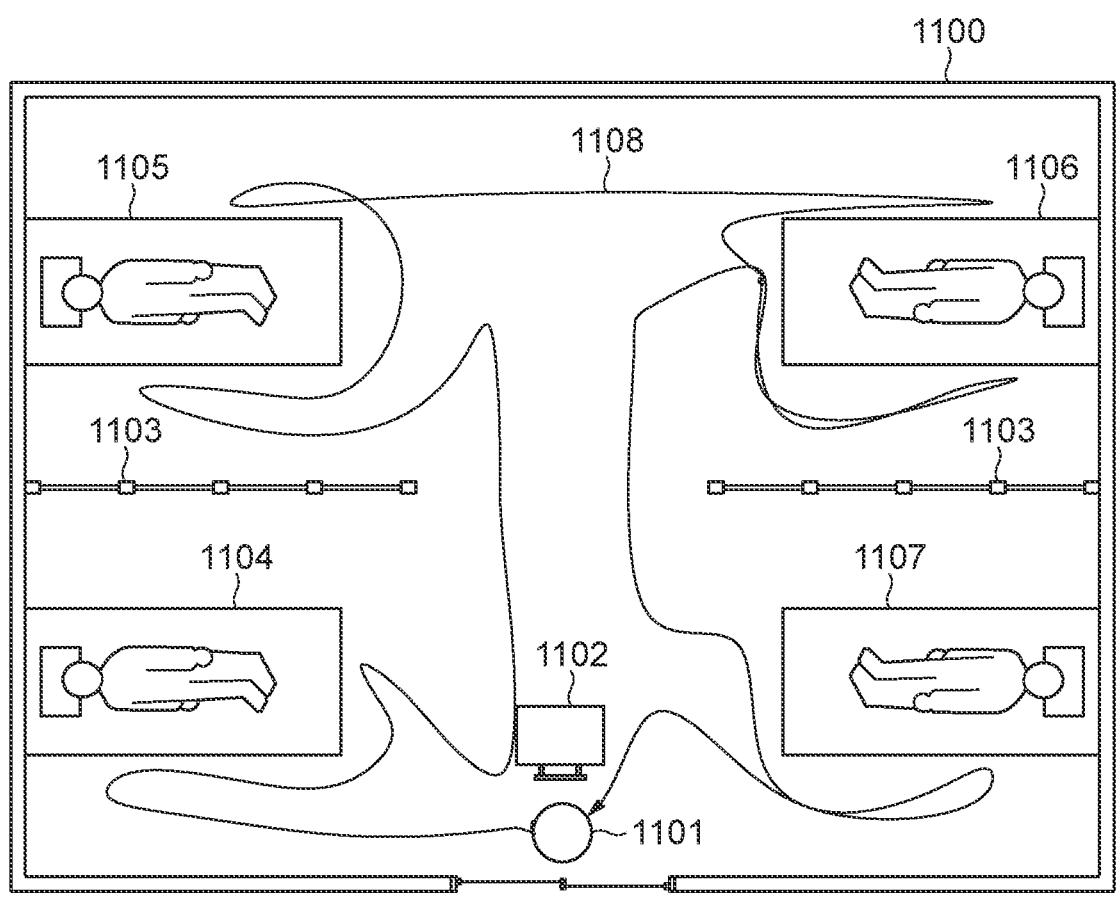
FIG. 11 is an overhead view showing a state in which a user photographs patients, one after another, using the system shown in FIG. 1, while making rounds in a large room.

FIG. 11 is an overhead view showing a state in which a user photographs patients, one after another, using the system 1 while making rounds in a large room 1100.

The examination process performed by the system 1 has been described in detail heretofore with reference to FIGS. 7 to 10, while referring to the notification UI 507 in FIG. 5 and the camera settings in FIG. 6. In FIG. 11, first, the meaning of each of reference numerals will be described. Then, there will be described advantageous effects assumed to be provided by the present embodiment in a case where the system 1 is used by a user (such as a nurse) to photograph patients in the large room 1100 while making rounds.

Note that the large room 1100 is a sickroom for a plurality of patients within a ward, and in the illustrated example in FIG. 11, the large room 1100 is for four patients.

The overhead view shown in FIG. 11 includes a user 1101, a nurse cart 1102, partition curtains 1103, patients 1104 to 1107, and a walking track 1108.

The user (such as a nurse) 1101 carries the image capturing apparatus 100 and the walking measurement device 101, walks rounds from one bed to another of the patients 1104 to 1107, and photographs an affected area of each of the patients 1104 to 1107 while communicating with the patient.

The nurse cart 1102 with casters can be smoothly moved in a horizontal direction and is used mainly for carrying necessary things, such as a laptop personal computer, the image capturing apparatus 100, a sphygmomanometer, and disinfection liquid, when making rounds. In the present embodiment, a case where it is determined in the step S806 that the image capturing apparatus 100 is in the horizontally moving state corresponds to a case where the user 1101 is moving with the nurse cart 1102 and the image capturing apparatus 100 placed thereon.

The partition curtains 1103 are used for protecting privacy between the patients 1104 to 1107 hospitalized in the large room 1100.

The patient 1104 to 1107 are lying on their respective medical beds arranged in the large room 1100. For example, assuming that each medical bed has a size of 200×90 centimeters and a head side of the medical bed is in contact with a wall of the large room 1100 as shown in FIG. 11, the user 1101 cannot walk along the head side of the medical bed. Therefore, the longest distance by which the user 1101 walks along one medical bed in the large room is 490 centimeters (200×2+90).

The walking track 1108 is one along which the user 1101 makes rounds in the large room 1100 while using the system 1. Note that the walking track 1108 is illustrated only as an example of a route along which the user 1101 makes rounds from one to another of the patients 1104 to 1107 in the large room 1100, and the walking track is not limited to the illustrated walking track 1108.

Next, there will be described a preferred example in which the user 1101 makes rounds to photograph the patients 1104 to 1107 in the large room 1100. In the illustrated example, when the user 1101 makes rounds, the user 1101 goes to the patient 1104, the patient 1105, the patient 1106, and the patient 1107 in the mentioned order.

First, the user 1101 walks to the head of the medical bed of the patient 1104. The user 1101 powers on the image capturing apparatus 100 while communicating with the patient 1104. At this time, the patient information of the patient 1104 has not been stored in the camera's internal storage medium yet, and hence the image capturing apparatus 100 cannot photograph an affected area of the patient 1104.

However, after the image capturing apparatus 100 has been powered on, when the user 1101 is communicating with the patient 1104 for a while without walking, the CPU 200 starts the photographing-time sequence and displays the live view on the display unit 203 of the image capturing apparatus 100. After this live view display has been started, the user 1101 adjusts the orientation of the image capturing apparatus 100 such that a barcode or the like indicative of patient information, which is printed on a wristband worn by the patient 1104, is included in this live view. With this, the patient information acquisition function of the image capturing apparatus 100 is started, and the patient information of the patient 1104 is stored in the camera's internal storage medium of the image capturing apparatus 100.

After that, the user 1101 photographs one image of the affected area of the patient 1104, at the place, and starts to walk to the feet of the patient 1104. At this time, when the user 1101 arrives at the feet of the patient 1104 and photographs an affected area again, the movement of the user 1101 matches none of the conditions of the number of steps, the walking time, and the horizontal movement, described in the walking detection determination process in FIG. 8, and hence the CPU 200 does not detect that the user 1101 has walked. Therefore, the notification UI 507 (see FIG. 5) is not displayed on the image capturing apparatus 100, and the user 1101 can continue the processing for storing, whenever an affected area of the patient 1104 is photographed, photographed image data in association with the patient information of the patient 1104.

Next, when the user 1101 starts to walk toward the patient 1105 with the nurse cart 1102 and the image capturing apparatus 100 placed thereon, the horizontal movement of the image capturing apparatus 100 is detected in the walking detection determination process described with reference to FIG. 8. In this case, after resetting the walking information in the camera's internal storage medium, the CPU 200 starts the notification-time sequence and displays the live view on the display unit 203 of the image capturing apparatus 100. Further, when the horizontal movement of the image capturing apparatus 100 is detected in the walking detection determination process in FIG. 8, the notification UI 507 (see FIG. 5) is displayed on the image capturing apparatus 100. This makes it possible to notify the user 1101 of a possibility that the patient to be imaged is changed.

When the user 1101 arrives at the head of the medical bed of the patient 1105, the user 1101 views the notification UI 507 displayed on the image capturing apparatus 100 and presses the setting delete button 509, which has a meaning of providing an instruction for deleting the setting of the patient information. With this, when the patient information of the patient 1104 is deleted from the camera's internal storage medium, the CPU 200 starts the photographing-time sequence again and displays the live view on the display unit 203 of the image capturing apparatus 100. After this live view display has been started, the user 1101 adjusts the orientation of the image capturing apparatus 100 such that a barcode or the like indicative of patient information, which is printed on a wristband worn by the patient 1105, is included in the live view. With this, the patient information acquisition function of the image capturing apparatus 100 is started, and the patient information of the patient 1105 is stored in the camera's internal storage medium of the image capturing apparatus 100.

After that, when the user 1101 finishes photographing of an affected area of the patient 1105, the user 1101 starts to walk toward the next patient 1106.

When the user 1101 arrives at the head of the medical bed of the patient 1106, the user 1101 starts preparation for photographing an affected area, such as changing of the body posture, while communicating with the patient. At this time, it is detected in the walking detection determination process in FIG. 8 that the user 1101 has walked, and the notification UI 507 (see FIG. 5) is displayed on the image capturing apparatus 100. However, by performing the setting delete determination process in FIG. 10, when the no-operation detection time after displaying the notification UI 507 becomes equal to or more than the threshold value (ten seconds in the present embodiment) (when no-operation continues for a predetermined time period or longer), the patient information of the patient 1105 is deleted from the camera's internal storage medium. After the patient information has been deleted, the CPU 200 restarts the photographing-time sequence and displays the live view on the display unit 203 of the image capturing apparatus 100. This makes it possible to prevent the user 1101 from making an error in the operation of registering the patient information. Further, since the live view has already been displayed on the image capturing apparatus 100, the user 1101 can quickly start the patient information acquisition function of the image capturing apparatus 100 and acquire the patient information of the patient 1106 from a barcode or the like on a wristband of the patient 1106.

After the user 1101 has finished the preparation for photographing the affected area of the patient 1106, such as changing of the body posture, the user 1101 adjusts the orientation of the image capturing apparatus 100 such that the barcode or the like on the wristband of the patient 1106 is included in the live view being displayed on the image capturing apparatus 100. This starts the patient information acquisition function of the image capturing apparatus 100, and the patient information of the patient 1106 is stored in the camera's internal storage medium of the image capturing apparatus 100.

Then, after photographing one image of the affected area of the patient 1106, when the user 1101 additionally reciprocates along a longitudinal side of the medical bed of the patient 1106 to change the body posture, the notification UI 507 (see FIG. 5) is displayed on the image capturing apparatus 100 although the patient whose affected area is to be photographed is not changed from the patient 1106. This is because the count of either of the number of steps and the walking time exceeds the threshold value in the walking detection determination process in FIG. 8, whereby it is detected that the user 1101 has walked. At this time, if the user 1101 presses the setting hold button 510 on the notification UI 507, for holding the set patient information, the user 1101 can continue photographing of the affected area of the patient 1106 while holding the patient information of the patient 1106 in the camera's internal storage medium. However, it is difficult to perform a finger operation on the touch panel display of the image capturing apparatus 100 with a single hand, and when a case is considered where the user 1101 assists the patient with another single hand of his/her to perform photographing, the operability is not high. In such a situation, for example, the user 1101 is only required to operate the release button 501 three times (threshold value indicated in the data 607) by his/her single hand. This terminates the display of the notification UI 507 with the patient information of the patient 1106 remaining held in the camera's internal storage medium, and the user 1101 is enabled to perform photographing by pressing the release button 501. Therefore, the user 1101 can easily continue photographing of the affected area of the patient 1106.

Finally, when the user 1101 starts to walk toward the patient 1107 with the nurse cart 1102 and the image capturing apparatus 100 placed thereon, the horizontal movement of the image capturing apparatus 100 is detected in the walking detection determination process in FIG. 8. In this case, after resetting the walking information in the camera's internal storage medium, the CPU 200 starts the notification-time sequence and displays the live view on the display unit 203 of the image capturing apparatus 100. Further, when the horizontal movement of the image capturing apparatus 100 is detected in the walking detection determination process in FIG. 8, the notification UI 507 (see FIG. 5) is displayed on the image capturing apparatus 100.

When the user 1101 arrives at the head of the medical bed of the patient 1105, the user 1101 views the notification UI 507 on the image capturing apparatus 100 but presses neither the setting delete button 509 nor the setting hold button 510 on the notification UI 507 but changes the photographing mode to change the brightness or the like. In this case, it is determined by the setting delete determination process in FIG. 10 that the photographing mode has been changed (YES to the step S1006), and the patient information of the patient 1106 is deleted from the camera's internal storage medium. After deletion of this patient information, the CPU 200 restarts the photographing-time sequence and displays the live view on the display unit 203 of the image capturing apparatus 100. With this, it is possible to easily delete the setting of the patient information by omitting the step of operating the setting delete buttons 509 or the setting hold button 510. Further, since the live view has already been displayed on the image capturing apparatus 100, the user 1101 can quickly start the patient information acquisition function of the image capturing apparatus 100 and acquire the patient information of the patient 1107 from a barcode or the like on a wristband of the patient 1107.

After changing the photographing mode, the user 1101 adjusts the orientation of the image capturing apparatus 100 such that the barcode or the like on the wristband of the patient 1107 is included in the live view displayed on the image capturing apparatus 100. With this, the patient information acquisition function of the image capturing apparatus 100 is started, and the patient information of the patient 1107 is stored in the camera's internal storage medium of the image capturing apparatus 100.

Then, after the photographing of an affected area of the patient 1107 is finished, the user 1101 leaves the large room 1100.

As described above, even in a case where a user photographs patients, one after another, while making rounds indoors, such as in the large room 1100, where it is difficult to acquire the GPS information, the image capturing apparatus 100 can detect from the walking movement with high accuracy that the patient to be photographed has changed and notify the user of this fact. Further, the image capturing apparatus 100 prevents an error in an registration operation for associating photographed image data of an affected area of a patient and patient information, by inhibiting the user from photographing the affected area of the patient, after the notification until a specific operation or movement of the user is detected.

Note that although in the present embodiment, the patient information is acquired from a barcode on a wristband of a patient, other information, such as medical information, may also be acquired at the same time.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)TM), a flash memory device, a memory card, and the like.

Therefore, the present invention can also be realized by a program code itself supplied to and installed in a computer to cause the computer to realize the functions of the present invention. That is, the computer programs themselves for realizing the functions of the present invention are included in the present invention.

In this case, any program format, such as an object code, a program executed by an interpreter, and script data supplied to an OS, can be used insofar as it has the function of the program.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2021-212511 filed Dec. 27, 2021, which is hereby incorporated by reference herein in its entirety.

What is claimed is:

1. An electric equipment that has a function of acquiring patient information of an identifier according to an operation by a user and storing the acquired patient information in a storage medium, a function of generating photographed image data through photographing according to an operation by the user, and a function of storing the photographed image data in association with the patient information stored in the storage medium, comprising:
   at least one processor; and
   a memory coupled to the at least one processor, the memory having instructions that, when executed by the processor, configure the processor of the electric equipment to:
   acquire walking information of a walk of the user;
   perform notification to the user based on the walking information;
   stop photographing by an image capturing operation based on the walking information;
   delete the patient information from the storage medium based on an operation by the user in response to the notification; and
   terminate the notification in a case where the patient information is deleted from the storage medium.

2. The electric equipment according to claim 1, wherein the walking information is the number of steps or walking time of the user, after photographing according to the operation by the user.

3. The electric equipment according to claim 1, wherein the instructions which, when executed by the processor, further configure the processor of the electric equipment to detect a walk of the user, and
   wherein the walking information is based on a result of the detection.

4. The electric equipment according to claim 1, wherein the instructions which, when executed by the processor, further configure the processor of the electric equipment to communicate with an external device that detects a walk of the user, and
   wherein the walking information is based on a result of the detection by the external device, which is received from the external device.

5. The electric equipment according to claim 1, wherein the instructions which, when executed by the processor, further configure the processor of the electric equipment to detect horizontal movement, and
   wherein the notification is performed based on the detection of the horizontal movement.

6. The electric equipment according to claim 1, wherein the patient information is deleted based on an operation for a deletion instructing button to receive an instruction for deleting the patient information from the storage medium.

7. The electric equipment according to claim 1, wherein the patient information is deleted based on an operation for changing a photographing mode of the electric equipment.

8. The electric equipment according to claim 1, wherein in a case where no operation is detected for a predetermined time period or longer after the notification, the patient information is deleted from the storage medium.

9. The electric equipment according to claim 1, wherein the instructions which, when executed by the processor, further configure the processor of the electric equipment to acquire second walking information which is the number of steps or walking time of a walk of the user performed after the notification, and wherein the patient information is deleted based on the second walking information.

10. The electric equipment according to claim 1, wherein in a case where another operation is performed after the notification, the notification is terminated, in a state in which the patient information is stored in the storage medium.

11. The electric equipment according to claim 1, wherein the patient information is not deleted based on another operation for a holding instructing button not to delete the patient information stored in the storage medium, and wherein the photographed image data is stored in association with the patient information stored in the storage medium after the notification.

12. The electric equipment according to claim 11, wherein the another operation is a predetermined number or more of times of the image capturing operation during the notification.

13. A method of controlling an electric equipment that has a function of acquiring patient information of an identifier according to an operation by a user and storing the acquired patient information in a storage medium, a function of generating photographed image data through photographing according to an operation by the user, and a function of storing the photographed image data in association with the patient information stored in the storage medium, comprising:

acquiring walking information of a walk of the user;

performing notification to the user based on the walking information;

stopping photographing by an image capturing operation based on the walking information;

deleting the patient information from the storage medium based on an operation by the user in response to the notification; and terminating the notification in a case where the patient information is deleted from the storage medium.

14. A non-transitory computer-readable storage medium storing a program for causing a computer to execute a method of controlling an electric equipment that has a function of acquiring patient information of an identifier according to an operation by a user and storing the acquired patient information in a storage medium, a function of generating photographed image data through photographing according to an operation by the user, and a function of storing the photographed image data in association with the patient information stored in the storage medium, wherein the method comprises:

acquiring walking information of a walk of the user;

performing notification to the user based on the walking information;

stopping photographing by an image capturing operation based on the walking information;

deleting the patient information from the storage medium based on an operation by the user in response to the notification; and terminating the notification in a case where the patient information is deleted from the storage medium.

* * * * *